United States Patent [19]

Igaki

[11] Patent Number: 5,766,188

[45] Date of Patent: Jun. 16, 1998

[54] MEDICAL SUTURING MATERIAL

[75] Inventor: Keiji Igaki, Shiga, Japan

[73] Assignee: Kabushikikaisha Igaki Iryo Sekkei, Shiga, Japan

[21] Appl. No.: 765,942

[22] PCT Filed: May 8, 1996

[86] PCT No.: PCT/JP96/01220

§ 371 Date: Jan. 2, 1997

§ 102(e) Date: Jan. 2, 1997

[87] PCT Pub. No.: WO96/35377

PCT Pub. Date: Nov. 14, 1996

[30] Foreign Application Priority Data

May 8, 1995 [JP] Japan .................. 7-109833

[51] Int. Cl.$^6$ ................................ A61B 17/08

[52] U.S. Cl. ................. 606/151; 606/139; 606/213; 606/215; 606/142

[58] Field of Search ............... 606/151, 139, 606/213, 215, 219, 220, 142, 143; 227/175.1–182, 19, 901

[56] References Cited

U.S. PATENT DOCUMENTS 4,834,090  5/1989  Moore ..................... 128/303
5,397,324  3/1995  Carroll et al. ............. 606/139

FOREIGN PATENT DOCUMENTS

| 0577 373 A2 | 6/1992 | European Pat. Off. | ...... A61B 17/115 |
| 0667 119 A1 | 8/1995 | European Pat. Off. | ........ A61B 17/00 |
| 195 19 334 A1 | 12/1995 | Germany | ................ A61F 13/00 |
| 7-33342 | 6/1995 | Japan | ................ A61L 17/00 |
| 8-47526 | 2/1996 | Japan | ................ A61L 17/00 |

Primary Examiner—Michael Buiz
Assistant Examiner—Tina T. D. Pham
Attorney, Agent, or Firm—Limbach & Limbach L.L.P.

[57] ABSTRACT

A medical suturing material which is loaded into an automatic suturing device having a staple line when used. The medical suturing material has a main suturing material on which a shape maintaining support member made of a film or a sheet having rigidity is superposed, wherein the main suturing material and the shape maintaining support member are joined together by sewing by using a single thread into a bag shape and the leading end of the bag structure is closed so as to be loaded into the automatic suturing device having the staple line. The main suturing material is unwoven fabric such as felt, woven fabric or a knit cloth having some flexibility and stretchability. In particular, bioabsorbable polymer, such as polyglycolic acid or a portion of a tissue of an organism is employed.

5 Claims, 4 Drawing Sheets

MEDICAL SUTURING MATERIAL

TECHNICAL FIELD

The present invention relates to a medical suturing material which is sutured to, for example, an excised portion of a tissue of an organism, and more particularly, to an medical suturing material of a type arranged to be loaded into an automatic suturing device.

BACKGROUND ART

Excision of a diseased part of a tissue of an organism generally is performed by a surgical operation. In order to reduce burden of a patient, the operation has been performed with an endoscope.

For example, an excision operation using an automatic suturing device has been performed. The automatic suturing device is introduced into the organism through a perforation to excise the diseased part and suture the excised portion. By using the medical suturing material, an advantage can be realized in that the necessity of incision of the diseased part can be eliminated. Therefore, the automatic suturing device has, at the leading end thereof, a suturing mechanism portion for holding the excised portion of the tissue of an organism. Moreover, the suturing mechanism portion has a plurality of staple lines for performing the suturing operation and a cutting mechanism, such as a knife, for cutting the tissue of an organism.

As a matter of course, use of the automatic suturing device in the surgical operation is advantageous in shortening the time required to complete the suturing and incision operations and in simplifying the operation.

In a case where the automatic suturing device is used when an operation of a weak tissue, such as the lung, the branch, the liver, the alimentary canal or the like is performed, the suturing operation using the staples has a risk that the tissue tears. In a case of an operation of, for example, the lung, there is a risk that air leakage takes place. Since the air leakage is a fatal problem for the patient, reliable prevention is required.

Accordingly, a method has been employed in which a suturing material is previously loaded into the automatic suturing device so as to be sutured to the excised portion of the tissue of an organism.

In this case, a contrivance is required to enable the suturing material to be loaded into the automatic suturing device so as to reliably be brought to the diseased part. For example, a structure has been suggested in which a knit cloth having flexibility is placed on a felt-type suturing material, followed by sewing the two side lines with tacking threads to form a cylindrical shape.

However, the suturing material formed by sewing the knit cloth having flexibility with the sewing thread so as to be loaded into the automatic suturing device can be contracted into the direction of insertion when the automatic suturing device is inserted into the organism to be brought to the diseased part, thus resulting in the suturing material being displaced to the base portion of the automatic suturing device or being turned around the automatic suturing device. That is, a problem of twisting takes place.

If the suturing material is displaced or turned, appropriate treatment cannot smoothly be performed. In particular, an operation of a type which is performed with an endoscope encounters a critical problem.

DISCLOSURE OF THE INVENTION

In view of the foregoing, an object of the present invention is to provide a medical suturing material which is capable of preventing displacement and turn when an automatic suturing device is inserted, for example, capable of reliably preventing air leakage when used in an operation of the lung.

To achieve the foregoing object, a medical suturing material according to the present invention is loaded into an automatic suturing device having a staple line when used, the medical suturing material including: a main suturing material on which a shape maintaining support member made of a film or a sheet having rigidity is superposed, wherein the main suturing material and the shape maintaining support member are joined together by sewing by using suturing threads along the two widthwise side ends thereof to be formed into a cylindrical shape so as to be loaded into the automatic suturing device having the staple line.

The suturing material according to the present invention has the main suturing material which may be a material, such as unwoven fabric such as felt, woven fabric or a knit cloth if it has somewhat flexibility and stretchability. A known material may be employed. In consideration of the state after the operation, it is preferable that bioabsorbable polymer, such as polyglycolic acid, or a portion of a tissue of an organism, for example, the organ protective film, such as the heart sac, be employed.

The shape maintaining support member is made of a material having rigidity which cannot be deformed even somewhat heavy load is applied. For example, plastic, metal or paper formed into a sheet or a film is employed.

The shape maintaining support member cannot be deformed even applied with external force. Therefore, the suturing material formed by the shape maintaining support member into a bag shape is free from displacement taking place attributable to shrinkage in the insertion direction when the automatic suturing device is inserted.

The suturing material is formed into a shape adaptable to the automatic suturing device by the shape maintaining support member and the shape can be maintained by the rigidity of the shape maintaining support member. Therefore, unintentional turn (twisting) can be prevented.

BEST MODE FOR CARRYING OUT THE INVENTION

Preferred embodiments of the present invention will now be described in detail with reference to the drawings.

Embodiment 1

Figure 1:
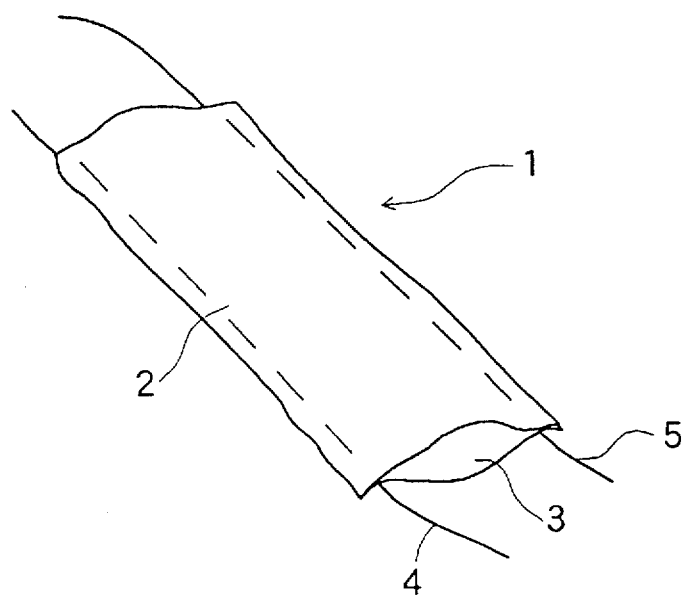
FIG. 1 is a schematic perspective view showing an example of a suturing material according to the present invention.

A medical suturing material 1 according to this embodiment, as shown in FIG. 1, is formed by combining one main suturing material 2 made of felt (for example, NEOVEIL which is trade name of Gunze Kabushiki Kaisha) composed of, for example absorbable polyglycolic acid and a shape maintaining support member 3 in the form of a plastic sheet by sewing.

The main suturing material 2 may be a known suturing material as well as the bioabsorbable polymer, such as the absorbable polyglycolic acid. For example, a portion of a tissue of an organism, such as an organ protective film exemplified by the heart sac, may be employed.

Also the shape maintaining support member 3 is not limited to the plastic sheet. A material, such as a metal sheet or paper, having somewhat rigidity, may be employed.

Each of the main suturing material 2 and shape maintaining support member 3 is formed into an elongated shape having a length which is substantially the same as that of a loading portion of an automatic suturing device to be described later. The main suturing material 2 and shape maintaining support member 3 are connected to each other by sewing with two suturing threads 4 and 5 along the widthwise side portions thereof.

It is preferable that the suturing threads 4 and 5 be so-called monofilaments in view of easy drawing, while the material of the same may be determined arbitrarily. For example, an bioabsorbable polymer thread or a polyamide thread (a so-called nylon thread) having excellent sliding characteristic may preferably be employed.

The ends of the suturing threads 4 and 5 may be made as it is so as to individually be removed from the main suturing material 2 and shape maintaining support member 3 after the sewing operation has been completed. As an alternative to this, a stopper, such as a knot, may be formed at an end adjacent to the shape maintaining support member 3 to enable the suturing threads 4 and 5 to be removed simultaneously with removal of the shape maintaining support member 3 after the sewing operation has been completed.

Assuming that the width of the main suturing material 2 is W1 and that of the shape maintaining support member 3 is W2, a relationship W1<W2 is held in this embodiment. That is, the shape maintaining support member 3 is wider than the main suturing material 2.

The reason for this is that the main suturing material 2 is placed in the holding surface of the automatic suturing device and the rear side is covered with the shape maintaining support member 3 to stabilize the state of loading. As a result, turn of the material can be prevented when it is loaded into the automatic suturing device.

Figure 2:
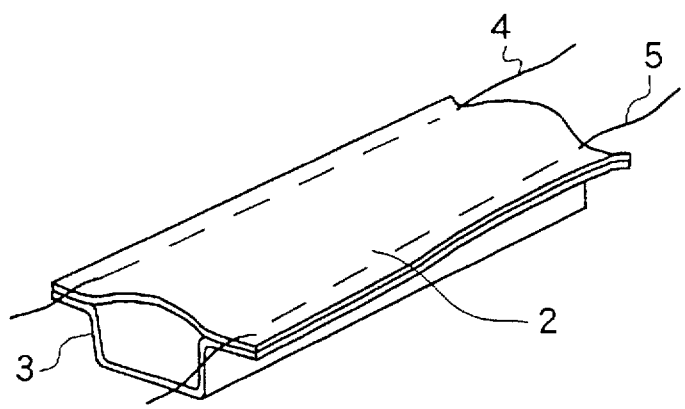
FIG. 2 is a schematic perspective view showing another example of the suturing material according to the present invention.

In particular, when the shape maintaining support member 3 made of the plastic sheet is, as shown in FIG. 2, subjected to a bending work to have an outer shape which coincides with the loading portion of the automatic suturing device, the state of loading can significantly be stabilized. Thus, the turn can reliably be prevented.

As a matter of course, the structure is not limited to this. A structure may be employed in which, for example, the width of the main suturing material 2 is made to be larger than that of the shape maintaining support member 3 to somewhat cover the shape maintaining support member 3.

The medical suturing material having the above-mentioned structure is loaded into the automatic suturing device. The structure of the automatic suturing device and the method to use the medical suturing material according to this embodiment will now be described.

Figure 3:
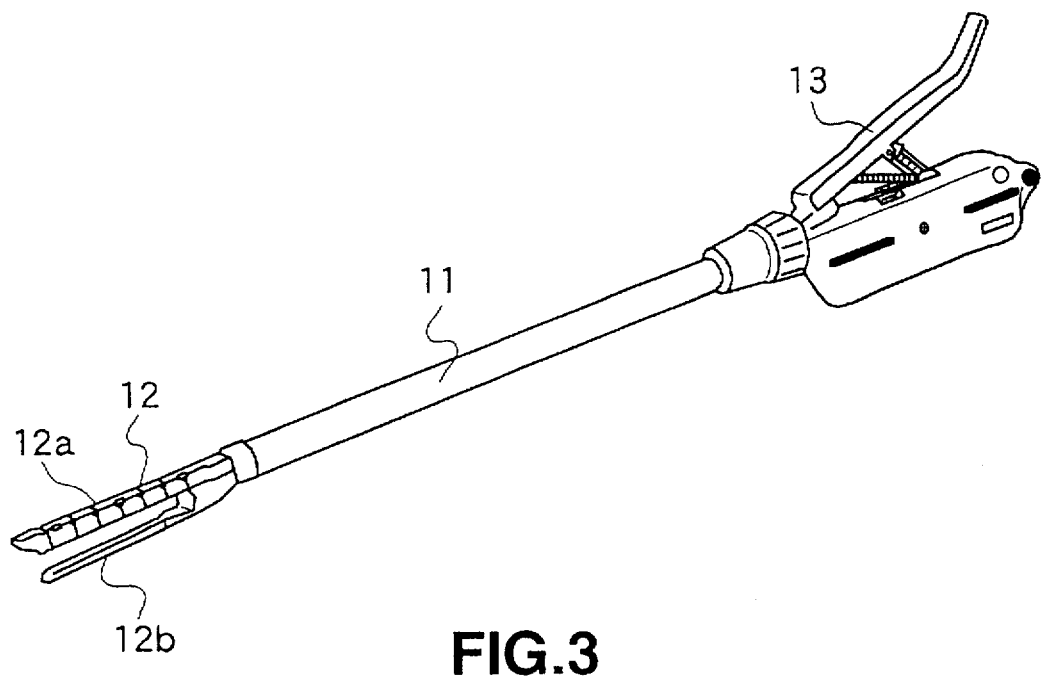
FIG. 3 is a schematic perspective view showing an example of an automatic suturing device in which the suturing material is used.

As shown in FIG. 3, the automatic suturing device has, at the leading end of a shaft 11 thereof, a suturing portion 12 which can be opened/closed. The automatic suturing device has, in the base portion thereof, an operation portion 13 which is arranged to be held and with which operation of the automatic suturing device is performed.

Figure 4:
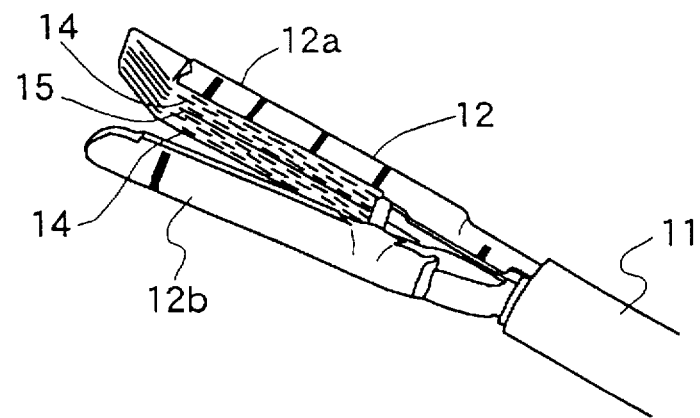
FIG. 4 is a schematic plan view showing an essential portion of a suturing mechanism portion of the automatic suturing device.

As shown in FIG. 4, the suturing portion 12 has a suturing mechanism portion 12a on which a cartridge accommodating staples and a knife blade are mounted; and a jaw portion 12b for holding a tissue of an organism. A plurality of (3 lines×3 lines=6 lines) of staple lines 14 and knife scanning line 15 face the holding surface of the suturing mechanism portion 12a.

The automatic suturing device is introduced into the organism through an attachment called a "surge boat". That is, the surge boat is attached to a perforation formed in the organism, and then the shaft 11 of the automatic suturing device is inserted into the organism through the surge port. As a result, the perforation formed in the organism can be sealed up.

Figure 5:
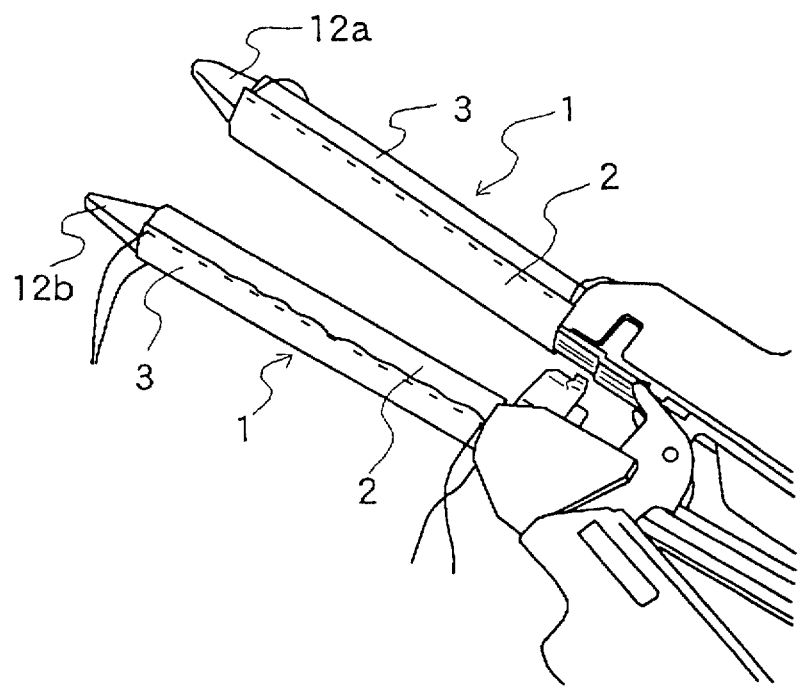
FIG. 5 is a schematic perspective view showing a state where the suturing material has been loaded into the automatic suturing device.

The medical suturing material 1 is loaded into the suturing portion 12 of the automatic suturing device when used. FIG. 5 shows a state where the suturing material 1 has been loaded into the suture portion 12 of the automatic suturing device such that the suturing material 1 is attached to the suturing mechanism portion 12a and jaw portion 12b.

The suturing material 1 can smoothly be loaded into the suture portion 12 by sliding the suture portion 12 along the shape maintaining support member 3 made of a plastic sheet. In a case where the shape maintaining support member 3 is bent to have a rectangular shape to coincide with the shape of the suture portion 12, loading can easily be performed by using the rear flat surface.

In the above-mentioned state, the automatic suturing device is inserted into the organism through the surge boat as described above to be brought to the diseased part. Since the suturing material 1, to be loaded into the automatic suturing device, has a shape reinforced by the shape maintaining support member 3 at this time, displacement and twisting can be prevented.

Figure 6:
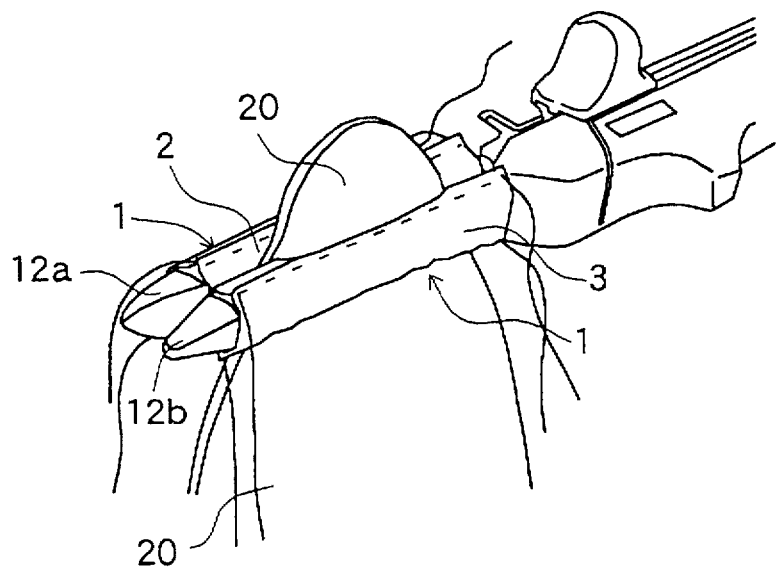
FIG. 6 is a schematic perspective view showing a state of a suturing operation by using the automatic suturing device.

After the suture portion 12 has been introduced into the diseased part, the excised portion of the tissue of an organism 20 is held by the suturing mechanism portion 12a and jaw portion 12b, as shown in FIG. 6. As a result, the excised portion is covered with the main suturing material 2.

Then, an operation lever 13a provided for the operation portion 13 of the automatic suturing device is operated so that staples are driven through the operation portion 13.

As a result, the staples are driven along the excised portion of the tissue of the organism 20 so that the suturing treatment is performed. Simultaneously, the main suturing material 2 of the suturing material 1 loaded into the suture portion 12 is pressed against the excised portion of the tissue of the organism 20 so as to be sutured by the staples.

The main suturing material 2 serves as a reinforcing member when the suturing operation is performed. By suturing the cut portion of the tissue of the organism 20 through the main suturing material 2, tearing of the tissue can be prevented. Thus, for example, an excision operation of a great sacculus alveolaris can be performed without air leakage.

Then, the knife provided for the suturing mechanism portion 12a is scanned along the scanning lines 15 to cut the tissue of the organism 20 and the main suturing material 2.

After the suturing operation has been performed, the automatic suturing device is removed, and excess portions, that is, the shape maintaining support member 3 is removed from the organism. The shape maintaining support member 3 can be removed by removing the suturing threads 4 and 5 connecting the main suturing material 2 and the shape maintaining support member 3 to each other by sewing so that they are removed. Then, the shape maintaining support member 3 is removed from the organism. In the case where the stopper, such as a knot, is provided for the end adjacent to the shape maintaining support member 3, the suturing threads 4 and 5 may be removed simultaneously with removal of the shape maintaining support member 3 after the suturing operation has been completed.

Figure 7:
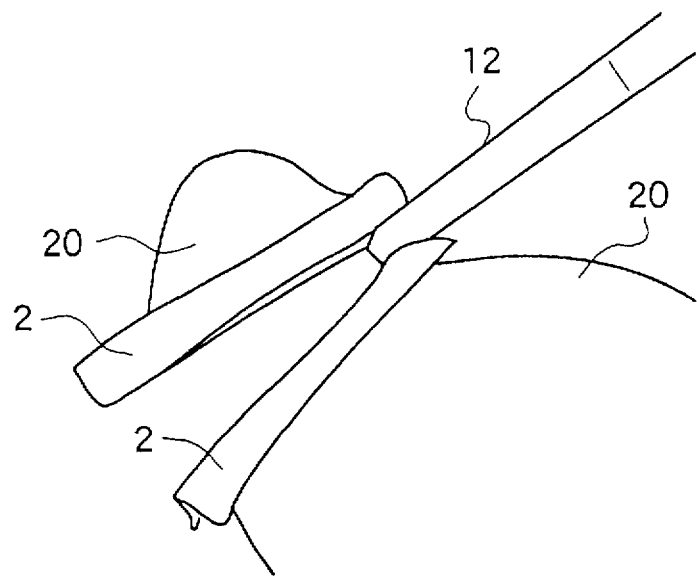
FIG. 7 is a schematic perspective view showing a state where the suturing treatment has been completed.

Thus, the suturing treatment is completed. By using the suturing material 1 according to this embodiment, the suturing operation can smoothly be performed. Moreover, the sutured portion can reliably be reinforced and air leakage from the same can be prevented. FIG. 7 shows a state of completion of the suturing operation, in which the main suturing material 2 is joined to the sutured portion of the tissue of the organism 20 by the suturing operation. The state of suturing can significantly be stabilized.

Although the invention has been described in its preferred form with a certain degree of particularity, it is understood that the present disclosure of the preferred form can be changed in the details of construction and in the combination and arrangement of parts.

Figure 8:
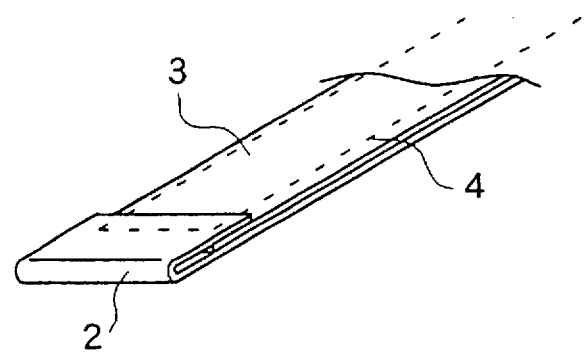
FIG. 8 is a schematic perspective view showing another example of the suturing material according to the present invention in which an end is closed.

Although the above-mentioned embodiment has the structure such that the two ends of the suturing material 1 formed by sewing the main suturing material 2 and the shape maintaining support member 3 are opened, a bag shape may be formed by sewing such that the end of the main suturing material 2 or the shape maintaining support member 3 is folded back and the leading end is closed by one suturing thread 4, as shown in FIG. 8. In a case where the leading end is closed, the suturing material 1 is pushed in by the automatic suturing device when it is loaded into the automatic suturing device so as to be inserted into the organism. As a result, displacement of the suturing material 1 can further reliably be prevented.

INDUSTRIAL APPLICABILITY

Since the suturing material according to the present invention has the structure such that the main suturing material having flexibility is supported by the support member having somewhat rigidity, displacement, twisting and the like taking place attributable to shrinkage generated when the automatic suturing device is inserted can be prevented.

Therefore, use of the suturing material according to the present invention enables the sutured portion to be reinforced reliably. As a result, tearing of the tissue and air leakage can be prevented.

I claim:

1. A medical suturing material which is loaded into an automatic suturing device having a staple line when used, said medical suturing material comprising:

a main suturing material made of at least one material selected from a group consisting of unwoven fabric, woven fabric and a knit cloth on which a shape maintaining support member made of a film or a sheet having rigidity is superposed, wherein said main suturing material and said shape maintaining support member are joined together by sewing by using a single thread into a bag shape and the leading end of the bag structure is closed so as to be loaded into the automatic suturing device having the staple line.

2. A medical suturing material according to claim 1, wherein said main suturing material is an bioabsorbable polymer.

3. A medical suturing material according to claim 2, wherein said bioabsorbable polymer is polyglycolic acid.

4. A medical suturing material according to claim 1, wherein said main suturing material is a portion of a tissue of an organism.

5. A medical suturing material according to claim 1, wherein said tissue of an organism is the organ protective film.

* * * * *